United States Patent [19]
Grützke et al.

[11] Patent Number: 5,648,475
[45] Date of Patent: Jul. 15, 1997

[54] PROCESS FOR PREPARING ALKYL GLYCOSIDES HAVING A LOW DEGREE OF GLYCOSIDATION

[75] Inventors: Jürgen Grützke, Bochum; Stefan Schmidt, Haltern, both of Germany

[73] Assignee: Huels Aktiengesellschaft, Marl, Germany

[21] Appl. No.: 524,530

[22] Filed: Sep. 7, 1995

[30] Foreign Application Priority Data

Sep. 7, 1994 [DE] Germany .................. 44 31 854.5

[51] Int. Cl.$^6$ ................................ C07H 1/00
[52] U.S. Cl. ........................... 536/18.6; 536/124
[58] Field of Search ................... 536/18.5, 124

[56] References Cited

U.S. PATENT DOCUMENTS

| | | | |
|---|---|---|---|
| 4,996,306 | 2/1991 | McDaniel, Jr. et al. | 536/18.6 |
| 5,206,357 | 4/1993 | Schmidt | 536/18.6 |
| 5,227,480 | 7/1993 | Oberholz et al. | 536/18.5 |
| 5,420,262 | 5/1995 | Schmidt | 536/18.5 |
| 5,461,144 | 10/1995 | Kahsnitz et al. | 536/18.6 |

FOREIGN PATENT DOCUMENTS

| | | |
|---|---|---|
| 0362671 | 4/1990 | European Pat. Off. . |
| 0495174 | 7/1992 | European Pat. Off. . |
| 0501032 | 9/1992 | European Pat. Off. . |
| 0514627 | 11/1992 | European Pat. Off. . |
| 0514628 | 11/1992 | European Pat. Off. . |
| 4129587 | 3/1993 | Germany . |
| WO93/10133 | 5/1993 | WIPO . |

*Primary Examiner*—Elli Peselev
*Attorney, Agent, or Firm*—Oblon, Spivak, McClelland, Maier & Neustadt, P.C.

[57] ABSTRACT

In a process for preparing alkyl glycosides having $C_8$ to $C_{20}$ alkyl radicals by glycosidation and transglycosidation or by direct glycosidation, a saccharide syrup having a dextrose equivalent of 90 to 95 is used as starting material. Products having a very low mean degree of glycosidation are achieved by filtering off oligosaccharide during the reaction and/or afterwards.

21 Claims, No Drawings

PROCESS FOR PREPARING ALKYL GLYCOSIDES HAVING A LOW DEGREE OF GLYCOSIDATION

BACKGROUND OF THE INVENTION

1. Field of the Invention

The invention relates to a novel single- or two-stage process for preparing alkyl glycosides having $C_8$ to $C_{20}$ alkyl radicals and having a mean degree of glycosidation between 1.05 and 1.4.

2. Discussion of the Background

Alkyl glycosides having $C_8$ to $C_{20}$ alkyl groups can be prepared in whole or in part from renewable raw materials. Therefore, and also because of their very good biodegradability, they are becoming increasingly important. The products, in addition to their surfactant properties of interest, have the advantage that their polarity can be set exactly via the length of the alkyl chain and the degree of glycosidation. Because of this the alkyl glycosides can be specifically directed to their field of application.

In EP-A-0 495 174, a direct glycosidation of saccharides using $C_{12}$ to $C_{20}$ alcohols is described. In this single stage preparation of alkyl polyglycosides, sodium hypophosphite is added for color enhancement. Products are obtained here having mean degrees of glycosidation of 1 to 8. However, the preparation process is restricted to starting mixtures having a very low water content. It cannot, therefore, be carried out using an inexpensive syrup.

In the two-stage alkyl glycoside preparation, a glycosidation is first carried out, alkyl glycosides having short-chain alkyl groups being prepared from saccharides and $C_2$ to $C_6$ alcohols. These products are then converted into the desired alkyl glycosides having surfactant properties in the second stage by transglycosidation using $C_8$ to $C_{20}$ alcohols.

This preparation route has long been known. Recent applications in this sector frequently relate to the preparation of products improved in color. In these cases reducing agents are sometimes added or special equipment is sometimes used.

Thus in EP-A-0 501 032, the glycosidation is performed in an evaporator. The glucose syrup preferably used there is generally a starch hydrolysate containing oligosaccharides. The dextrose equivalent of such syrups is usually 90 to 95. The alkyl polyglycosides having long-chain alkyl groups prepared here preferably have mean degrees of glycosidation in the range from 1.3 to 5, a value of 1.65 being specified in the example.

According to EP-A-0 514 628, the transglycosidation can also be performed in an evaporator. In EP-A-0 514 627, the transglycosidation is carried out in a reaction column. A molar ratio of alkyl glycoside having a short alkyl radical to long-chain alcohol of 1:2 to 1:15 is set in this case and alkyl polyglycosides having degrees of glycosidation of preferably 1.2 to 3 are obtained.

WO 93/101 33 describes a two-stage process for preparing alkyl oligoglycosides, which can be carried out continuously or discontinuously and in which a glucose syrup having a monomeric glucose content of 90 to 100% is used. The process described here is highly complex overall. It requires a secondary reaction both in the glycosidation and also in the transglycosidation. Moreover, in both of the reaction stages narrow temperature ranges must be maintained. WO 93/101 33 furnishes alkyl oligoglucosides having a polyglucose content of less than 5 per cent by weight.

To separate off by distillation the fatty alcohols from alkyl polyglycosides having $C_{10}$ to $C_{18}$ alkyl groups and a mean degree of glycosidation of 1.05 to 1.4, according to DE-A-41 29 587, a thin-layer evaporator is used. The preparation of the alkyl polyglycosides is not considered in more detail there.

The publications mentioned do not give any indication as to how alkyl glycosides having a mean degree of glycosidation between 1.05 and 1.4 can be prepared in a simple manner.

The object of the present invention was therefore to provide a simple and inexpensive process for preparing alkyl glycosides having $C_8$ to $C_{20}$ alkyl radicals and having a mean degree of glycosidation between 1.05 and 1.4. The products, furthermore, are also to show a good color quality.

SUMMARY OF THE INVENTION

The object is achieved according to the invention by the fact that a saccharide syrup having a dextrose equivalent of 90 to 95 is used and, moreover, oligosaccharide is filtered off during and/or after the reaction.

Surprisingly, by means of these measures, products of high color quality having a low degree of glycosidation are successfully prepared, for example in simple stirred tank cascades.

Without the filtration, solid, insoluble constituents are virtually unavoidable in the alcoholic reaction mixtures which comprise partially alkylated sugar oligomers and block piping and reactors. The separation of these oligosaccharides surprisingly has a strong effect on the mean degree of glycosidation.

DETAILED DESCRIPTION OF THE PREFERRED EMBODIMENTS

Preferably, the filtration is carried out using filters having pore sizes from 50 to 200 μm, filters having pore sizes from 80 to 100 μm being very particularly preferably used.

For the process, syrups of, for example, glucose, mannose, galactose, glucose, allose or talose can be used.

Preferably, a glucose syrup is used here. The syrup can contain 10 to 70% water. A water content of 10 to 40% are preferred here.

To characterize the monosaccharides, the content of reducing sugars, calculated as dextrose on the basis of dry matter, is determined and termed dextrose equivalent. According to this, a pure monosaccharide has a dextrose equivalent of 100, while dextrose equivalents below 100 indicate a content of oligosaccharides. According to the invention, the dextrose equivalent is preferably 93 to 95.

In the two-stage preparation, for the glycosidation $C_2$ to $C_6$ alcohols, such as ethanol, n-propanol, isopropanol, n-butanol, t-butanol, amyl alcohol or hexanol are used.

Monosaccharide and $C_2$ to $C_6$ alcohol are preferably reacted in a molar ratio of 1:5 to 1:10.

The alkyl glycosides having $C_2$ to $C_6$ alkyl chains prepared in the glycosidation are reacted with $C_2$ to $C_{20}$ fatty alcohols in a second stage, the transglycosidation. The fatty alcohols in this stage can be linear or branched. They can also contain olefinic double bonds. Natural or synthetic fatty alcohols or fatty alcohol mixtures can be used. Examples which may be mentioned are octanol, decanol, 10-undecen-1-ol, dodecanol, myristyl alcohol and stearyl alcohol. Preferably, fatty alcohols having 10 to 16 C atoms are used. The alkyl glycoside having $C_2$ to $C_6$ alkyl groups is usually reacted with the fatty alcohol in a molar ratio of 1:4 to 1:10.

Preferably, the fatty alcohol is preheated to 80 to 150° C. and very particularly preferably to 100° to 130° C. The reaction temperature in the transglycosidation is usually 60° to 140° C. and in particular 80 to 120° C.

In the direct glycosidation, the same saccharides and fatty alcohols are used as in the two-stage preparation. The saccharide/fatty alcohol molar ratio in this case is usually in the range from 1:4 to 1:10. Preferably, by direct glycosidation, alkyl glycosides having $C_8$ to $C_{14}$ alkyl radicals are prepared.

In the single- and two-stage preparation, the acid catalysts used can be mineral acids such as sulfuric acid or hydrochloric acid. Organic acids are also very suitable, such as arylsulphonic, alkylsulphonic or aralkylsulphonic acids. The reaction temperature in this case is generally in the range from 100° to 140° C. The glycosidation is preferably carried out at 100° to 125° C. In the transglycosidation and in the direct glycosidation the reaction temperature is usually 105° to 135° C., vacuum generally being applied to accelerate the reaction.

The single- and two-stage preparation of the alkyl glycosides can be performed continuously or discontinuously. The continuous alkyl glycoside synthesis is usually carried out in a stirred-tank cascade, in which case the stirred tanks can also be partly or completely replaced by reaction columns or tubular reactors.

In the two-stage alkyl glycoside preparation, filtration is preferably carried out after each stage. In the direct glycosidation filtration is preferably only performed after the reaction. In cascades of reactors, filtration can be carried out in the lines between the reactors and in the case of reactors equipped with circuits, filtration can also be carried out in these circuits.

The alkyl glycoside dissolved in fatty alcohol arising at the end of the reaction is neutralized with suitable bases in a known manner. The excess fatty alcohol is then separated off by distillation which can be performed in a thin-layer evaporator or short-path evaporator. The alkyl glycoside obtained which preferably has a mean degree of glycosidation of 1.1 to 1.3 is then mixed with water and bleached using peroxide. The end product has an iodine color value (ICV) of below 20 and preferably has a residual fatty alcohol content less than 1%.

The process according to the invention leads to reaction mixtures having a very low content of undissolved constituents. Cracking which can impair the color of the product does not occur. Piping the reactors do not have a tendency to blockages. This increases the operational safety and the service life of the reactors. At the same time, alkyl glycosides having a low degree of glycosidation are directly obtained as are used advantageously in detergents and dishwashing agents.

Obviously, numerous modifications and variations of the present invention are possible in light of the above teachings. It is therefore to be understood that within the scope of the appended claims, the invention may be practice otherwise than as specifically describe therein.

This application is based on German Patent Application P 44 31 854.5, filed in the German Patent Office on Sept. 7, 1994, the entire contents of which are hereby incorporated by reference.

What is claimed as new and desired to be secured by Letters Patent of the United States is:

1. A process for the preparation of an alkyl glycoside having $C_8$ to $C_{20}$ alkyl groups and a mean degree of glycosidation of between 1.05 and 1.4, comprising glycosidating by reacting a saccharide syrup having a dextrose equivalent of 90 to 95 with an alcohol, and filtering off oligosaccharide present during the preparation.

2. The process of claim 1, wherein filters having a pore size from 50 to 200 μm are used in the filtration.

3. The process of claim 2, wherein said filters have a pore size of from 80 to 100 μm.

4. The process of claim 1, wherein said saccharide syrup is a glucose syrup.

5. The process of claim 1, wherein alkyl glycosides having a mean degree of glycosidation from 1.1 to 1.3 are prepared.

6. The process of claim 1, wherein a glycosidation molar ratio is 1:5 to 1:10.

7. The process of claim 1, wherein a $C_{10}$ to $C_{14}$ fatty alcohol is used.

8. The process of claim 1, wherein a glycosidation temperature is 100° to 140° C.

9. The process of claim 1, wherein a glycosidation temperature is 100° to 125° C.

10. The process of claim 1, wherein said saccharide syrup is selected from the group consisting of glucose, mannose, galactose, glucose, allose, talose and a mixture thereof.

11. The process of claim 1, wherein either said glycosidation, said transglycosidation or both are conducted in the presence of an acid catalyst.

12. A process for preparing alkyl glycosides having $C_8$ to $C_{20}$ alkyl radicals and a mean degree of glycosidation of 1.05 to 1.4 by glycosidation and transglycosidation including:

a) glycosidating an alcohol with a monosaccharide having a dextrose equivalent of 90 to 95 to form an alkyl glycoside;

b) transglycosidating the alkyl glycoside with a fatty alcohol; and c) filtering off oligosaccharide present during the preparation.

13. The process of claim 12, wherein filters having a pore size from 50 to 200 μm are used in the filtration.

14. The process of claim 13, wherein said filters have a pore size of from 80 to 100 μm.

15. The process of claim 12, wherein said saccharide syrup is a glucose syrup.

16. The process of claim 12, wherein alkyl glycosides having a mean degree of glycosidation from 1.1 to 1.3 are prepared.

17. The process of claim 12, wherein a glycosidation molar ratio is 1:5 to 1:10 and a transglycosidation molar ratio is 1:4 to 1:10.

18. The process of claim 12, wherein a $C_{10}$ to $C_{14}$ fatty alcohol is used.

19. The process of claim 12, wherein a glycosidation temperature is 100° to 140° C.

20. The process of claim 12, wherein a glycosidation temperature is 100° to 125° and a transglycosidation temperature is 105° to 135° C.

21. The process of claim 1, wherein said saccharide is selected from the group consisting of glucose, mannose, galactose, glucose, allose, talose and a mixture thereof.

* * * * *